United States Patent [19]

Suzuki

[11] 4,087,470
[45] * May 2, 1978

[54] PROCESS FOR THE PRODUCTION OF ETHYLENE GLYCOL

[75] Inventor: Shigeto Suzuki, San Francisco, Calif.

[73] Assignee: Chevron Research Company, San Francisco, Calif.

[*] Notice: The portion of the term of this patent subsequent to Oct. 7, 1992, has been disclaimed.

[21] Appl. No.: 699,099

[22] Filed: Jun. 23, 1976

[51] Int. Cl.² .......................................... C07C 31/18
[52] U.S. Cl. ............................... 568/864; 260/449 M
[58] Field of Search ....................... 260/635 D, 449 M

[56] References Cited

U.S. PATENT DOCUMENTS

| 2,285,448 | 6/1942 | Loder | 260/635 D |
| 3,911,003 | 10/1975 | Suzuki | 260/635 D |
| 3,930,812 | 1/1976 | Harris et al. | 260/449 M |

Primary Examiner—James O. Thomas, Jr.
Assistant Examiner—G. T. Breitenstein
Attorney, Agent, or Firm—D. A. Newell; John Stoner, Jr.; W. Keith Turner

[57] ABSTRACT

A cyclic process for producing ethylene glycol comprising the steps of:

(1) contacting formaldehyde with a synthesis gas comprising carbon monoxide and hydrogen in the presence of a catalytic amount of hydrogen fluoride under conditions effective to deplete carbon monoxide from the synthesis gas and produce glycolic acid and diglycolic acid;

(2) contacting the acid product of step (1) with ethylene glycol, diethylene glycol, or mixtures thereof under conditions effective to produce ethylene glycol glycolate and diglycolate, diethylene glycol glycolate and diglycolate, or mixtures thereof;

(3) removing residual carbon monoxide from the carbon monoxide depleted synthesis gas of step (1) thereby producing a hydrogen rich gas;

(4) contacting the glycolate and diglycolate product of step (2) with the hydrogen-rich gas mixture of step (3) under conditions effective to produce ethylene glycol, diethylene glycol, or mixtures thereof; and (5) recycling from step (4) to step (2) an amount of the glycol product effective to esterify substantially all the acid product present in the reaction zone of step (2).

8 Claims, 2 Drawing Figures

CRUDE PRODUCT DISTILLATION AND RECYCLE

CYCLIC PROCESS FOR PREPARING ETHYLENE GLYCOL

PROCESS FOR THE PRODUCTION OF ETHYLENE GLYCOL

BACKGROUND OF THE INVENTION

The process of this invention concerns the production of ethylene glycol from formaldehyde and a synthesis gas comprising carbon monoxide and hydrogen. More particularly, this invention provides a multiple-step process for producing ethylene glycol. The principal steps involve (1) production of glycolic and diglycolic acids and simultaneous separation of carbon monoxide and hydrogen in synthesis gas, (2) esterification of the acid product, and (3) reduction of the esters. In addition to the integrated reaction steps, the process utilizes specific recycling steps to enhance the efficiency of the esterification and hydrogenation reactions.

Commonly assigned U.S. Pat. No. 3,911,003 granted Oct. 7, 1975 describes an improved process for producing glycolic acid and diglycolic acid from formaldehyde and carbon monoxide employing a hydrogen fluoride catalyst. According to the disclosure, in cases where the glycolic acid product is intended as a feedstock in the production of ethylene glycol, the acid is esterified with methanol and then catalytically hydrogenated to produce ethylene glycol. While the chemistry of this procedure is satisfactory, it has been found that the economics of the process presents a problem for large scale commercial exploitation. The substantial cost of methanol esterification and hydrogenation is not entirely offset by the improved yields and reaction rates obtained through the use of a hydrogen fluoride catalyst.

Accordingly, it remains desirable to provide an effective process for preparing ethylene glycol from formaldehyde and a synthesis gas comprising carbon monoxide and hydrogen.

SUMMARY OF THE INVENTION

It has now been found that a process for preparing ethylene glycol which comprises the steps of (1) contacting formaldehyde and a synthesis gas comprising carbon monoxide and hydrogen in the presence of hydrogen fluoride under conditions effective to deplete carbon monoxide from the synthesis gas and simultaneously form glycolic and diglycolic acids; (2) contacting the acid product of step (1) with ethylene glycol, diethylene glycol, or mixtures thereof under conditions effective to produce ethylene glycol glycolate and diglycolate, diethylene glycol glycolate and diglycolate, or mixtures thereof; (3) removing residual carbon monoxide from the carbon monoxide depleted synthesis gas of step (1) to produce a hydrogen-rich gas; (4) contacting the glycolate and diglycolate product of step (2) with the hydrogen-rich gas mixture of step (3) under conditions effective to produce ethylene glycol or diethylene glycol; and (5) recycling a portion of the glycol product from step (4) to step (2) economically achieves high yields of ethylene glycol.

BRIEF DESCRIPTION OF THE FIGURES

The several features of the present process will become more readily apparent from the following detailed description of the invention taken in conjunction with the accompanying figures.

DETAILED DESCRIPTION OF THE INVENTION

Figure 1:
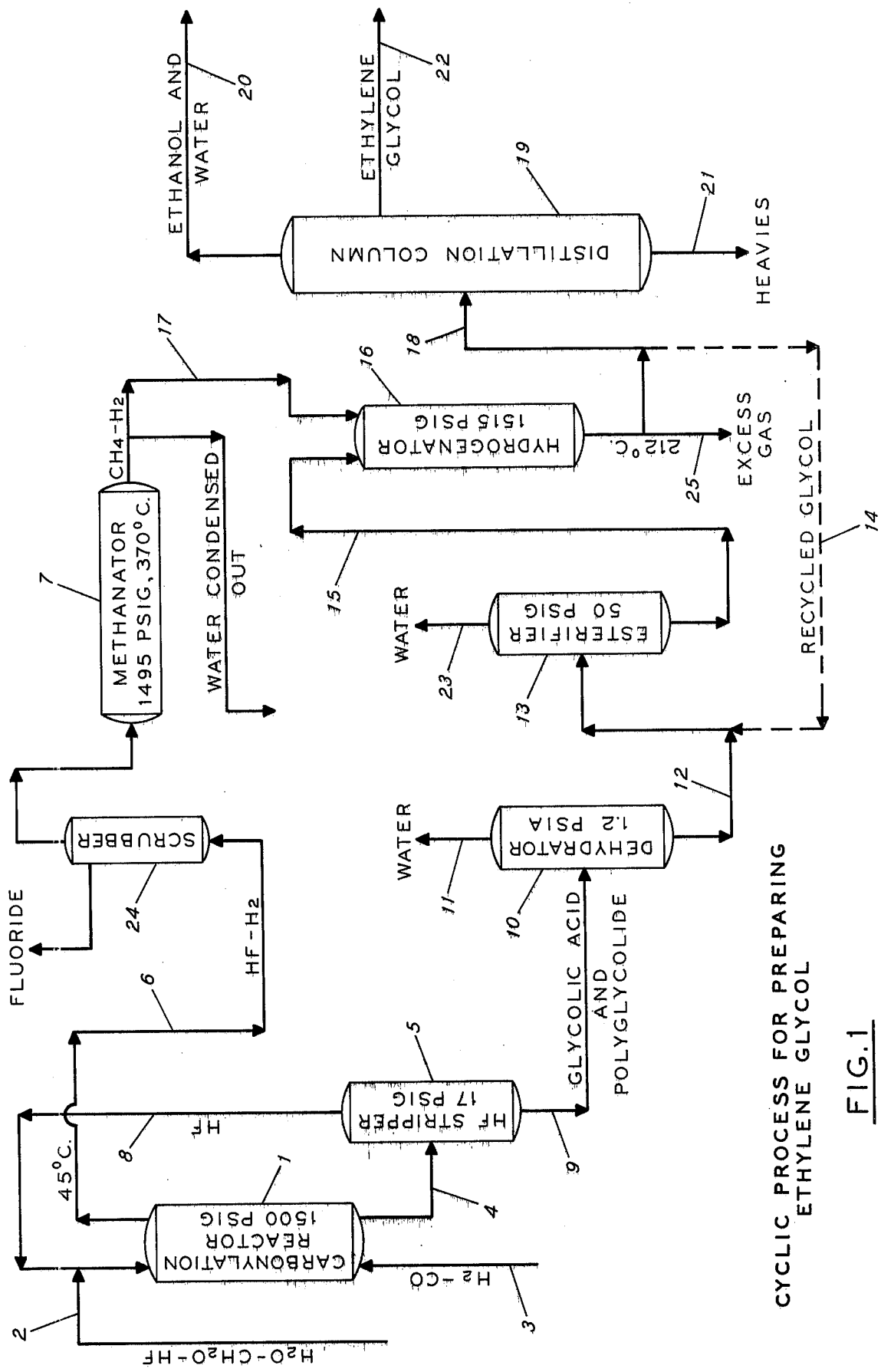
FIG. 1 illustrates in flow-sheet form a preferred embodiment of the process of this invention.

The present invention provides an economical cyclic process for producing high yields of ethylene glycol at improved production rates. The process utilizes a carefully selected sequence of reactions employing particular reactants and reaction conditions, as well as recycle to achieve economical production rates and yields.

In the first step, a reaction zone is charged with formaldehyde, a synthesis gas comprising carbon monoxide and hydrogen, and hydrogen fluoride. The reaction zone is maintained under conditions which are effective to form diglycolic and glycolic acids, otherwise known as oxydiacetic and hydroxyacetic acids respectively.

Reaction conditions suitable for the production of glycolic acid include a temperature of from about 0° to about 100° C, preferable 0° to about 80° C, and a synthesis gas partial pressure between about 10 psig and about 4000 psig. Preferably the reaction is carried out in the presence of water, for example up to about 25 weight percent of water based on the total weight of formaldehyde, water and hydrogen fluoride catalyst. The presence of water increases the production of glycolic acid and decreases the production of diglycolic acid. In a particularly preferred embodiment of the process of this invention the temperature in the reaction zone is maintained between 20° C and 60° C and the synthesis gas partial pressure is maintained between 10 and 3000 psig. Typically the total pressure is not appreciably above the carbon monoxide and hydrogen partial pressures, carbon monoxide and hydrogen being by far the most volatile of the reactants and products. Usually the total pressure is about 1 to 10 percent higher than the carbon monoxide and hydrogen partial pressures.

Among other factors, the economic success of the process of this invention is attributable to the high yields of glycolic acid resulting from the use of a catalyst comprising hydrogen fluoride to promote the reaction of formaldehyde and carbon monoxide, at moderate temperatures and pressures. An important feature of this process is that by using a catalyst comprising HF, pressures are sufficiently low that raw synthesis gas having a hydrogen to carbon monoxide molar ratio of about 2:1 can be practically employed. While hydrogen fluoride, per se, is of course a satisfactory catalyst, other catalysts comprising hydrogen fluoride are also satisfactory. For example, commonly assigned copending U.S. Pat. application Ser. No. 572,780 filed Apr. 29, 1975 describes suitable catalysts comprising hydrogen fluoride and non-interfering constituents such as metal salts like copper oxides, silver oxide, nickel oxide and halogen acids such as HBr, HCl and HI. $HBF_4$ is a particularly preferred constituent.

In the presence of hydrogen fluoride, the reaction to produce glycolic acid is surprisingly rapid. The rate of reaction is so high that even at moderate temperatures in the range of 20° to 60° C the reaction is completed in relatively short reaction times. The low reaction temperatures which may be employed in the initial stage of the process of this invention minimize reactor corrosion, such that stainless steel reactors are satisfactory. At higher temperatures more expensive materials such as Monel, Hastelloy alloys or titanium are required.

Preferably, the ratio of condensed reactants and catalyst is maintained such that in excess of 0.5 mol of hydrogen fluoride are present per mol of formaldehyde. Suitable hydrogen fluoride to formaldehyde mol ratios range from 1:2 to about 4:1, preferably 7:3. Expressed on a weight basis the overall ratio of reactants is suitably from about 5 to about 65 percent formaldehyde and from about 40 to about 95 percent catalyst with a partial pressure of carbon monoxide ranging from about 10 to about 4000 psig. More preferable ranges are from 5 to about 40 percent formaldehyde and 45 to about 85 percent catalyst. The rate of reaction is most rapid at the higher proportions of catalyst in the reaction mixture.

The synthesis gas stream to the reaction zone can be passed either concurrently or countercurrently to the formaldehyde stream. In a preferred embodiment the synthesis gas is passed countercurrently to the formaldehyde and catalyst so that the carbon monoxide is reacted out of the upward-flowing stream and a purified hydrogen-rich stream of reduced carbon monoxide content is obtained. In accordance with the cyclic nature of the process the carbon monoxide depleted stream is used in the subsequent hydrogenation described in detail hereinafter.

Crude glycolic acid and diglycolic acid are recovered from the first reaction zone. The crude acid contains catalyst which is preferably removed prior to esterification and recycled to the first reaction zone. The boiling point of hydrogen fluoride is 19.7° C at one atmosphere, which is considerably lower than that of diglycolic or glycolic acid. Thus, the hydrogen fluoride catalyst is readily separated by distillation and recycled to the reaction zone.

According to the present process the purified acid product is esterified with ethylene glycol, diethylene glycol, or a mixture of the two and hydrogenated to produce ethylene glycol and diethylene glycol. U.S. Pat. No. 2,285,448 granted June 9, 1942 describes the esterification and hydrogenation of glycolic acid. It has been found that prior to esterification it is desirable to dehydrate the glycolic acid by heating to a temperature of from about 120° C to about 200° C, preferable from about 150° to about 180° C under 0.1 to 0.2 atmospheric pressure. Glycolic acid possesses characteristics of both a carboxylic acid and an alcohol and is accordingly capable of forming linear esters by reaction between an alcohol group of one molecule and the carboxyl group of another with the simultaneous formation of water which is removed. These esters may take the form of monoglycolide or polyglycolides. Many of the glycolides of glycolic acid are solids at normal temperatures and pressures. However, they are soluble in hot ethylene glycol. As used hereinafter the term "anhydrous glycolic acid" includes the various dehydrated forms of the acid, and in particular a mixture of glycolic acid and polyglycolides.

Following dehydration, the anhydrous glycolic acid is contacted with ethylene glycol or diethylene glycol under conditions effective to produce the glycolate esters. Preferably complete esterification is achieved by adding hot ethylene or diethylene glycol and removing water formed during esterification until substantially all the carboxyl groups of the anhydrous acid are esterified. Suitable conditions for esterification include at temperature of from about 150° to about 250° C, preferably from about 170° to about 220° C, and a pressure of from about 0 psig to about 100 psig, preferably from about 0 psig to about 50 psig.

The glycol employed during esterification is preferably obtained as a recycled portion of the crude glycol product. The following reaction sequence illustrates that in theory 1 mol of ethylene glycol will combine with 1 mol of anhydrous glycolic acid to produce 2 mols of ethylene glycol, a fraction of which may be recycled to the esterification step and the remainder recovered as product. In practice, it is desirable to recycle sufficient ethylene glycol to insure a molar excess of alcohol during esterification. Suitable mol ratios of glycol to acid during esterification vary from about 1.5:1 to about 10:1, preferably from about 2:1 to about 6:1.

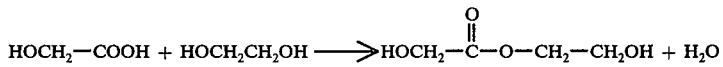

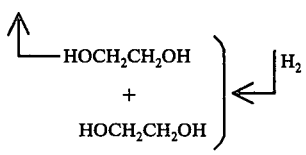

Having prepared the ester, the next step in the process, which is also illustrated by the reaction sequence depicted above, comprises hydrogenating the ester to produce glycol. The liquid phase hydrogenation can be conducted at temperatures from about 150° to about 300° C, preferably from about 200° to about 250° C and pressures from about 500 psig to about 5000 psig, preferably from about 1000 psig to about 2000 psig. Considerable latitude in the temperature of hydrogenation is possible depending upon the use and choice of hydrogenation catalyst. Metals and metal oxides are the preferable catalysts. Typical metal oxide catalysts include, for example, copper oxide-chromium oxide, or copper oxide in combination with the oxide of magnesium, barium, sodium, nickel, silver, lithium, potassium, cesium, zinc, cobalt and the like or mixtures thereof. A preferred catalyst comprises cobalt metal in combination with zinc and copper oxides.

As previously noted, the carbon monoxide-depleted hydrogen-rich stream from the first reaction zone provides a ready source of hydrogen for the ester hydrogenation reaction. However, carbon monoxide is a poison in ester hydrogenation reactions. Carbon monoxide can be removed by any of the known methods. A common method is to react carbon monoxide with some of the hydrogen to form methane over known commercial catalysts, usually nickel on an inert oxide or kieselguhr support. The hydrogen may also be purified by adsorption of the impurities in cyclic adsorption processes, or by cryogenic separation. Accordingly, the carbon monoxide-depleted stream is preferably passed to a hydrogenation vessel in order to convert remaining carbon monoxide to methane. Any of the conventional hydrogenation catalysts can be employed for this purpose. U.S. Pat. No. 3,930,812 granted Jan. 6, 1976, incorporated herein by reference, describes a typical hydrogenation of carbon oxides to methane.

The carbon monoxide depleted stream from the first reaction zone also contains some hydrogen fluoride catalyst. The catalyst may be removed by known methods. For example, catalyst may be removed by adsorption on NaF pellets to give a complex, from which the catalyst may be recovered for reuse.

Following hydrogenation, the ethylene glycol product is purified, for example by distillation to produce a refined commercial grade ethylene glycol.

The following Example is intended to further illustrate practice of the present invention. The example is not intended to limit the scope of the invention, inasmuch as various modifications and alternative embodiments of the principals of the invention will be readily apparent to those of ordinary skill in the art.

EXAMPLE

This Example illustrates a material balance for producing 200,000,000 lb/yr of ethylene glycol according to a preferred embodiment of the present cyclic process. Referring to FIG. 1, carbonylation reactor 1 is charged through line 2 with 12,960 lb/hr formaldehyde, 3884 lb/hr water and 570 lb/hr hydrogen fluoride; and through line 3 with synthesis gas comprising 14,056 lb/hr carbon monoxide and 3092 lb/hr hydrogen. Reactor 1 is operated at a temperature of from about 40° to 70° C and a pressure of about 1500 psig. Crude glycolic acid and hydrogen fluoride catalyst are passed from reactor 1 through line 4 to hydrogen fluoride stripper 5. Similarly carbon monoxide-depleted synthesis gas comprising 570 lb/hr HF, 3092 lb/hr $H_2$ and 1960 lb/hr CC is passed from reactor 1 through line 6 to scrubber 24 where any residual HF is removed. The purified gas is passed to methanator 7. 28,940 lb/hr of purified glycolic acid and polyglycolide are passed from stripper 5 to dehydrator 10 through line 9 wherein 1940 lb/hr water is removed through line 11. 27,000 lb/hr glycolic acid polymers are passed through line 12 to esterification vessel 13 which is simultaneously charged with 53,570 lb/hr recycled crude ethylene glycol through line 14. Esterification is conducted at a temperature of about 225° C and a pressure of about 50 psig. 1890 lb/hr water is distilled out through line 23. The ethylene glycol ester is passed through line 15 to an ester hydrogenation vessel 16. The hydrogenation vessel 16 is charged by 2,672 lb/hr $H_2$ and 1180 lb/hr methane from vessel 7 through line 17. Hydrogenation is conducted at a temperature of about 225° C and a pressure of about 1500 psig. Unused, excess hydrogen along with methane is passed out of the hydrogenator as a bleed gas stream via line 25. Crude ethylene glycol is passed from hydrogenator 16 through line 18 to distillation column 19. A portion of the product from line 18 is returned to the esterification vessel 13 by line 14 (dotted line in FIG. 1) and the remaining fraction is refined to give the ethylene glycol product. 776 lb/hr water, methanol, and ethanol and 690 lb/hr bottoms are removed from column 19 via lines 20 and 21 respectively. 25,345 lb/hr ethylene glycol product is recovered at line 22.

Figure 2:
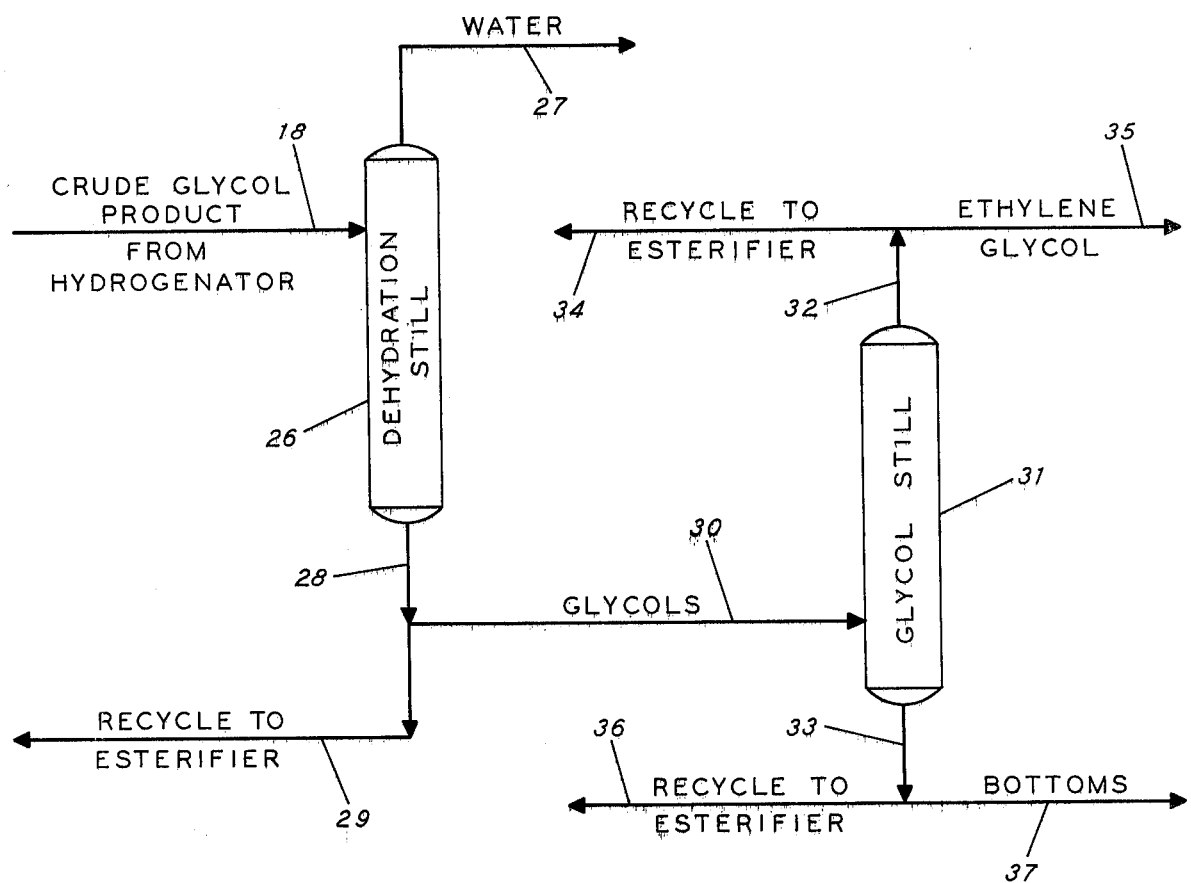
FIG. 2 illustrates a preferred product distillation scheme.

FIG. 2 illustrates a preferred modification of the process described in the Example. The modification provides alternative products for recycle to the esterification vessel. Referring to FIG. 2, crude glycol product from the hydrogenator is passed through line 18 to dehydration still 26. Water and ethanol are removed and pass out of the still 26 through line 27. Dehydrated crude product is recovered from the still at line 28. At this point, various products can be selected for recycle. Three cases best illustrate typical situations.

In the first case, if the hydrogenation is carried out under conditions where the conversion of glycolate in the hydrogenator is relatively high, the crude product in line 18 will comprise wet ethylene glycol and a minor amount of unconverted glycolate. A fraction of the dehydrated product in line 28 can be recycled to the esterifier via line 29 and the remainder refined to remove whatever unconverted glycolate is present; or, the dehydrated product in line 28 can be passed via line 30 to the glycol still 31. Still 31 separates the dehydrated glycol into an ethylene glycol overhead product passing through line 32 and a bottoms product passing through line 33. A fraction of the refined ethylene glycol in line 32 can be recycled via line 34 to the esterifier and the remainder recovered via line 35 as refined ethylene glycol product. Of course, a compromise of recycled fractions using lines 29 and 32 is also acceptable in this case.

In the second case, if the hydrogenation is carried out under conditions where the conversion of glycolate in the hydrogenator is relatively low, the crude product in line 18 will comprise wet ethylene glycol and unconverted glycolate. A fraction of the dehydrated product recovered through line 28 can be recycled to the esterifier, and the remaining fraction passed to the glycol still 31 via line 30. This latter fraction is separated in still 31 to produce a refined ethylene glycol recovered through line 32 and a bottoms comprising unconverted glycolate and heavies recovered through line 33. The bottoms can then be separated into a small bleed stream 37, and a large fraction which is recycled to the esterifier via line 36. Of course, if desired, additional ethylene glycol can be recycled via line 34 to supplement that of line 29.

In the third case, if diethylene glycol is the desired product for recycle, none of the dehydrated product in line 28 is recycled, as ethylene glycol would build up in the esterifier. The dehydrated product is passed through line 30 to still 31 where diethylene glycol is separated as a bottoms product and recycled via line 36.

Further modifications of the exemplified process can be made consistent with this invention as defined by the following claims.

What is claimed is:

1. A process for producing ethylene glycol which comprises the steps of: (1) contacting formaldehyde with a synthesis gas comprising carbon monoxide and hydrogen in the presence of hydrogen fluoride under conditions effective to deplete carbon monoxide from the synthesis gas and produce glycolic acid and diglycolic acid; (2) contacting the acid product of step (1) with ethylene glycol, diethylene glycol or mixtures thereof under conditions effective to produce ethylene glycol glycolates, diethylene glycol glycolates or mixtures thereof; (3) removing residual carbon monoxide and hydrogen fluoride from the carbon monoxide depleted synthesis gas of step (1) to produce a hydrogen-rich gas stream; (4) contacting the glycolate product of step (2) with the hydrogen-rich gas stream of step (3) under conditions effective to produce ethylene glycol or diethylene glycol; and (5) recycling sufficient glycol product from the product of step (4) to the esterification zone of step (2) so as to maintain a molar excess of glycol during esterification.

2. A process according to claim 1 wherein the source of hydrogen in hydrogenation step (4) is the carbon monoxide depleted hydrogen stream of step (1) which has been hydrogenated to form a hydrogen and methane mixture.

3. A process according to claim 1 wherein the formaldehyde and synthesis gas are contacted at a temperature between 0° and about 100° C and a carbon monoxide partial pressure between 10 psig and 4000 psig.

4. A process according to claim 1 wherein the formaldehyde and synthesis gas are contacted at a temperature between 20° and about 60° C and a carbon monoxide partial pressure between 10 psig and 3000 psig.

5. A process according to claim 1 wherein step (1) is carried out in the presence of water.

6. A process according to claim 1 wherein the acid product formed in step (1) is dehydrated prior to step (2) to form various anhydrous forms of glycolic acid.

7. A process according to claim 1 wherein the glycolic acid is contacted with ethylene glycol or diethylene glycol at a temperature of from about 150° to about 250° C and a pressure of from about 0 psig to about 100 psig.

8. A process according to claim 1 wherein the glycolate product is contacted with hydrogen at a temperature of from about 150° to about 300° C and a pressure of from about 500 psig to about 5000 psig, in the presence of a hydrogenation catalyst.

* * * * *